(12) United States Patent
Kawakami et al.

(10) Patent No.: US 10,064,764 B2
(45) Date of Patent: Sep. 4, 2018

(54) WEARING ARTICLE

(71) Applicant: UNICHARM CORPORATION, Ehime (JP)

(72) Inventors: Yusuke Kawakami, Kagawa (JP); Kazuya Fujimoto, Kagawa (JP)

(73) Assignee: Unicharm Corporation, Ehime (JP)

( * ) Notice: Subject to any disclaimer, the term of this patent is extended or adjusted under 35 U.S.C. 154(b) by 705 days.

(21) Appl. No.: 14/397,621

(22) PCT Filed: May 15, 2013

(86) PCT No.: PCT/JP2013/063604
§ 371 (c)(1),
(2) Date: Oct. 28, 2014

(87) PCT Pub. No.: WO2013/172392
PCT Pub. Date: Nov. 21, 2013

(65) Prior Publication Data
US 2015/0202095 A1    Jul. 23, 2015

(30) Foreign Application Priority Data

May 15, 2012 (JP) .................................. 2012-111950
Nov. 9, 2012 (JP) .................................. 2012-247918

(51) Int. Cl.
| A61F 13/539 | (2006.01) |
| A61F 13/49  | (2006.01) |
| A61F 13/496 | (2006.01) |

(52) U.S. Cl.
CPC ...... *A61F 13/49019* (2013.01); *A61F 13/496* (2013.01); *A61F 13/49011* (2013.01);
(Continued)

(58) Field of Classification Search
CPC ............ A61F 13/49058; A61F 13/4906; A61F 13/49061; A61F 13/4756; A61F 13/51108; A61F 2013/53778
(Continued)

(56) References Cited

U.S. PATENT DOCUMENTS 4,775,375 A    10/1988  Aledo
7,530,972 B2 *  5/2009  Ando ................ A61F 13/15593
                                                604/385.24
(Continued)

FOREIGN PATENT DOCUMENTS

EP    2 438 893 A1    4/2012
JP    2008-284190 A  11/2008
(Continued)

OTHER PUBLICATIONS

European extended Search Report from corresponding European application No. 13790577.4 dated Jan. 14, 2016 (6 pgs).
(Continued)

*Primary Examiner* — Susan Su
(74) *Attorney, Agent, or Firm* — Brinks Gilson & Lione (57) ABSTRACT

A wearing article making it possible to prevent a dimension in the transverse direction of respective recesses formed on an absorbent structure from being notably reduced even when the front and rear waist regions are disposed with waist elastic members directly or indirectly overlapping with the absorbent structure. The wearing article has a longitudinal direction parallel to a longitudinal center line, a transverse direction parallel to a transverse center line, a skin-facing surface and a non-skin-facing surface opposite to the skin-facing surface, and includes a chassis having a first waist region defined by one of front and rear waist regions and being elastically contractible in the transverse direction, a second waist region defined by another of the front and rear
(Continued)

waist regions and a crotch region lying between the front and rear waist regions, an absorbent structure disposed on the skin-facing surface of the chassis and extending in the longitudinal direction across the crotch region into at least the first waist region and recesses disposed on the absorbent structure, the absorbent structure includes a first region defined in the first waist region and the recesses at least partially lying in the first region and extending in the longitudinal direction; and a shape retention panel is disposed on the non-skin-facing surface of the first waist region so that the shape retention panel may indirectly or directly overlap the first region and the recesses as viewed in a thickness direction of the article.

7 Claims, 5 Drawing Sheets

(52) U.S. Cl.
CPC ............... *A61F 13/49012* (2013.01); *A61F 2013/49022* (2013.01); *A61F 2013/49068* (2013.01); *A61F 2013/49092* (2013.01)

(58) Field of Classification Search
USPC .................................................. 604/358–392
See application file for complete search history.

(56) References Cited

U.S. PATENT DOCUMENTS

| | | |
|---|---|---|
| 2004/0210204 A1 | 10/2004 | Shimada et al. |
| 2011/0098666 A1 | 4/2011 | Nakajima et al. |
| 2011/0098668 A1* | 4/2011 | Thorson ............ A61F 13/49012 604/385.25 |
| 2012/0143162 A1* | 6/2012 | Mukai ................ A61F 13/15804 604/385.3 |
| 2013/0041340 A1* | 2/2013 | Kawakami ........ A61F 13/49009 604/385.29 |
| 2013/0046266 A1 | 2/2013 | Kawakami |
| 2013/0226127 A1* | 8/2013 | Takahashi ......... A61F 13/15593 604/385.27 |
| 2013/0310785 A1* | 11/2013 | Wade ................. A61F 13/5622 604/385.3 |
| 2013/0338623 A1* | 12/2013 | Kinoshita ......... A61F 13/49011 604/385.29 |
| 2014/0358110 A1* | 12/2014 | Takahashi ............. A61F 13/496 604/385.29 |
| 2015/0238368 A1* | 8/2015 | Mukai ................... A61F 13/496 604/385.24 |

FOREIGN PATENT DOCUMENTS

| | | |
|---|---|---|
| JP | 2009-285196 A | 12/2009 |
| JP | 2011-125537 A | 6/2011 |
| JP | 2011-240054 A | 12/2011 |
| JP | 2012-016435 A | 1/2012 |
| JP | 2012-050744 | 3/2012 |

OTHER PUBLICATIONS

International Search Report from corresponding PCT application No. PCT/JP2013/063604 dated Aug. 20, 2013 (4 pgs).

* cited by examiner

WEARING ARTICLE

RELATED APPLICATION

This application is a 35 U.S.C. § 371 national phase filing of International Patent Application No. PCT/JP2013/063604, filed May 15, 2013, through which and to which priority is claimed under 35 U.S.C. § 119 to Japanese Patent Application Nos. 2012-111950, filed May 15, 2012 and 2012-247918, filed Nov. 9, 2012, the complete disclosures of which are hereby expressly incorporated herein by reference.

TECHNICAL FIELD

The present disclosure relates to wearing articles.

BACKGROUND

Conventionally, disposable wearing articles having an absorbent structure disposed with recesses are known. For example, Patent Literature 1 discloses a disposable diaper including an absorbent structure of which an absorbent core is formed with recesses extending in a longitudinal direction. The diaper disclosed therein has front and rear waist regions and a crotch region extending between these waist regions wherein the recesses extend across the crotch region into the front and rear waist regions. The front and rear waist regions are disposed, respectively, with a plurality of waist elastic members contractibly secured thereto under tension so as to extend in a transverse direction.

CITATION LIST

Patent Literature

{PTL 1}: JP 2012-16435 A

SUMMARY

Technical Problem

According to the disposable wearing article disclosed in Patent Literature 1, the waist elastic members are not present in the regions directly or indirectly overlapping with the absorbent structure and, for this reason, the contractile force of these elastic members do not act upon the absorbent structure. Consequently, the absorbent structure is apt to be spaced apart from the wearer's body, making it difficult to absorb body exudates sufficiently. It may be contemplated to overcome the problem by disposing the waist elastic members also in the region overlapping with the absorbent structure so that the waist elastic members may directly or indirectly overlap with the absorbent structure. However, such an arrangement will lead to another possibility that the absorbent structure might be contracted in the transverse direction and the recesses might be narrowed.

An object of the present invention is to improve the conventional wearing articles and to provide a wearing article making it possible to prevent the dimension in the transverse direction of the recess formed on the absorbent structure from being notably reduced even when the front and rear waist regions are disposed with the waist elastic members directly or indirectly overlapping with the absorbent structure.

Solution to Problem

The present invention relates to a wearing article having a longitudinal direction parallel to a longitudinal center line, a transverse direction parallel to a transverse center line, a skin-facing surface and a non-skin-facing surface opposite to the skin-facing surface, and including a chassis having a first waist region defined by one of front and rear waist regions and being elastically contractible in the transverse direction, a second waist region defined by another of the front and rear waist regions and a crotch region lying between the front and rear waist regions, an absorbent structure disposed on the skin-facing surface of the chassis and extending in the longitudinal direction across the crotch region into at least the first waist region and recesses disposed on the absorbent structure.

In the wearing article, the present invention lies in that the absorbent structure includes a first region defined in the first waist region and the recesses at least partially lying in the first region and extending in the longitudinal direction; and a shape retention panel is disposed on the non-skin-facing surface of the first waist region so that the shape retention panel indirectly or directly overlap the first region and the recesses as viewed in a thickness direction of the article.

Advantageous Effects of Invention

According to one or more particular embodiments of the present invention, the shape retention panel is disposed in the first waist region so as to overlap the recesses of the absorbent structure, thereby restricting the possibility that the recesses might be narrowed in the transverse direction.

DESCRIPTION OF EMBODIMENTS

Figure 1:
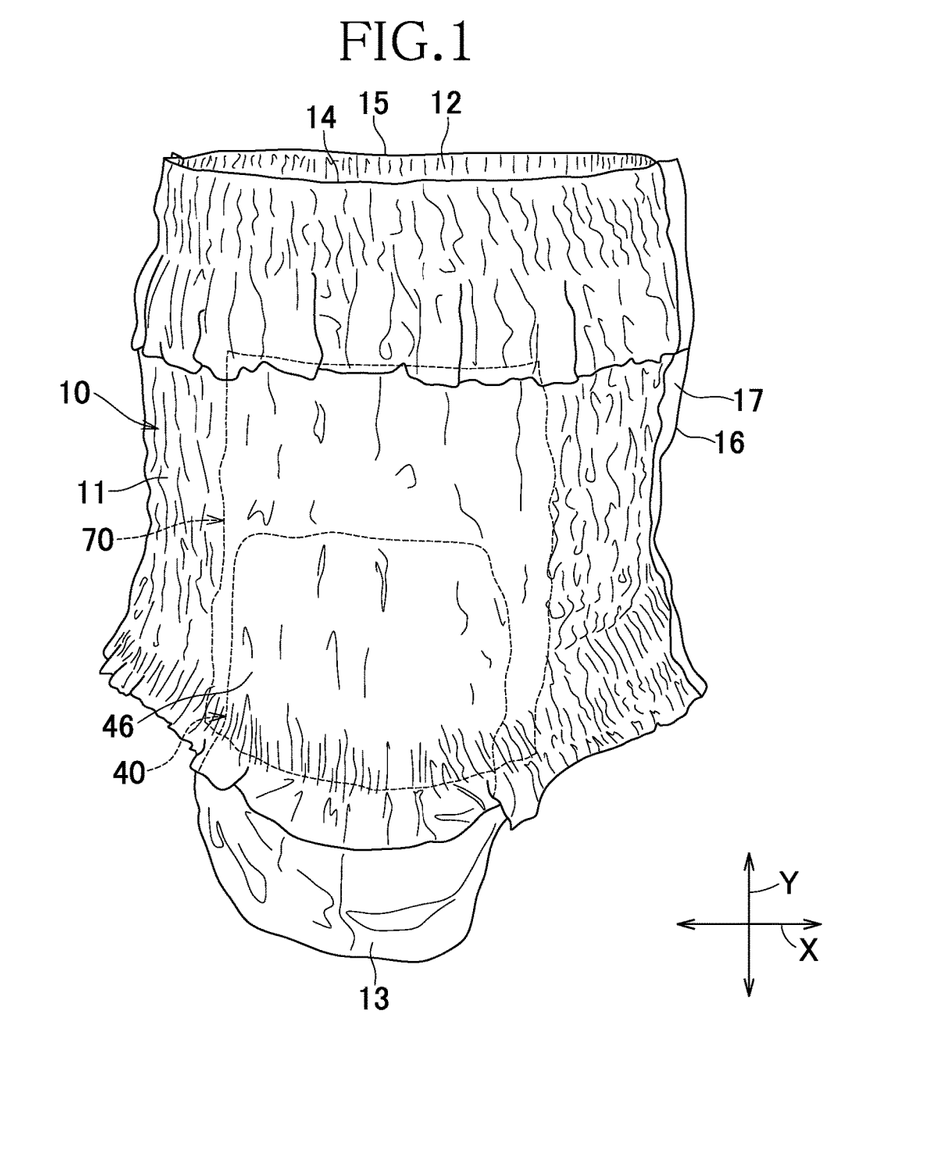
FIG. 1 is a perspective view of a disposable diaper as an example of a wearing article according to the present invention as viewed from the side of a front waist region.

Referring to FIG. 1, an illustrated disposable diaper according to an embodiment of the present invention has a longitudinal direction Y, a transverse direction X, front and rear end edges 14, 15 extending in the transverse direction X, both side edges 16 extending in the longitudinal direction Y, a skin facing surface and a non-skin facing surface and includes a chassis 10, an absorbent structure 40 disposed on the skin facing surface of the chassis 10 and a shape retention panel 70 overlapping with part of the absorbent structure 40. The chassis 10 includes a front waist region 11, a rear waist region 12, a crotch region 13 extending between the front and rear waist regions 11, 12 and seams 17 continually extending along the respective side edge portions 16. The front and rear waist regions 11, 12 are joined to each other along the seams 17 and thereupon a waist-opening is defined by the front and rear end edges 14, 15 and a pair of leg-openings is defined by both side edges 16 in the crotch region 13. After use of the diaper, the front and rear waist regions 11, 12 may be easily tear off from each other along the seams by the hands of a wearer or a helper.

Figure 2:
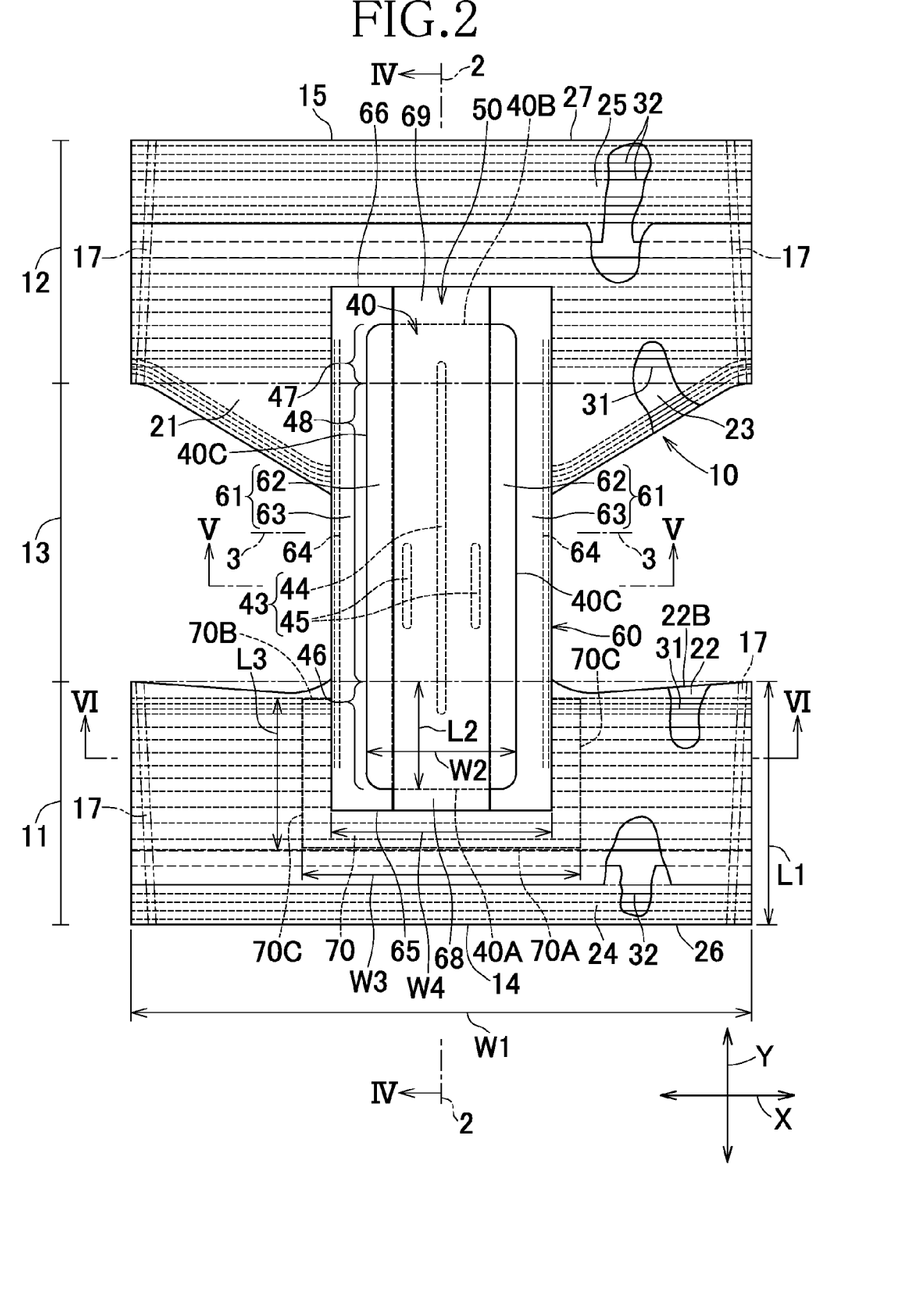
FIG. 2 is a flatly developed plan view of the disposable diaper.
Figure 3:
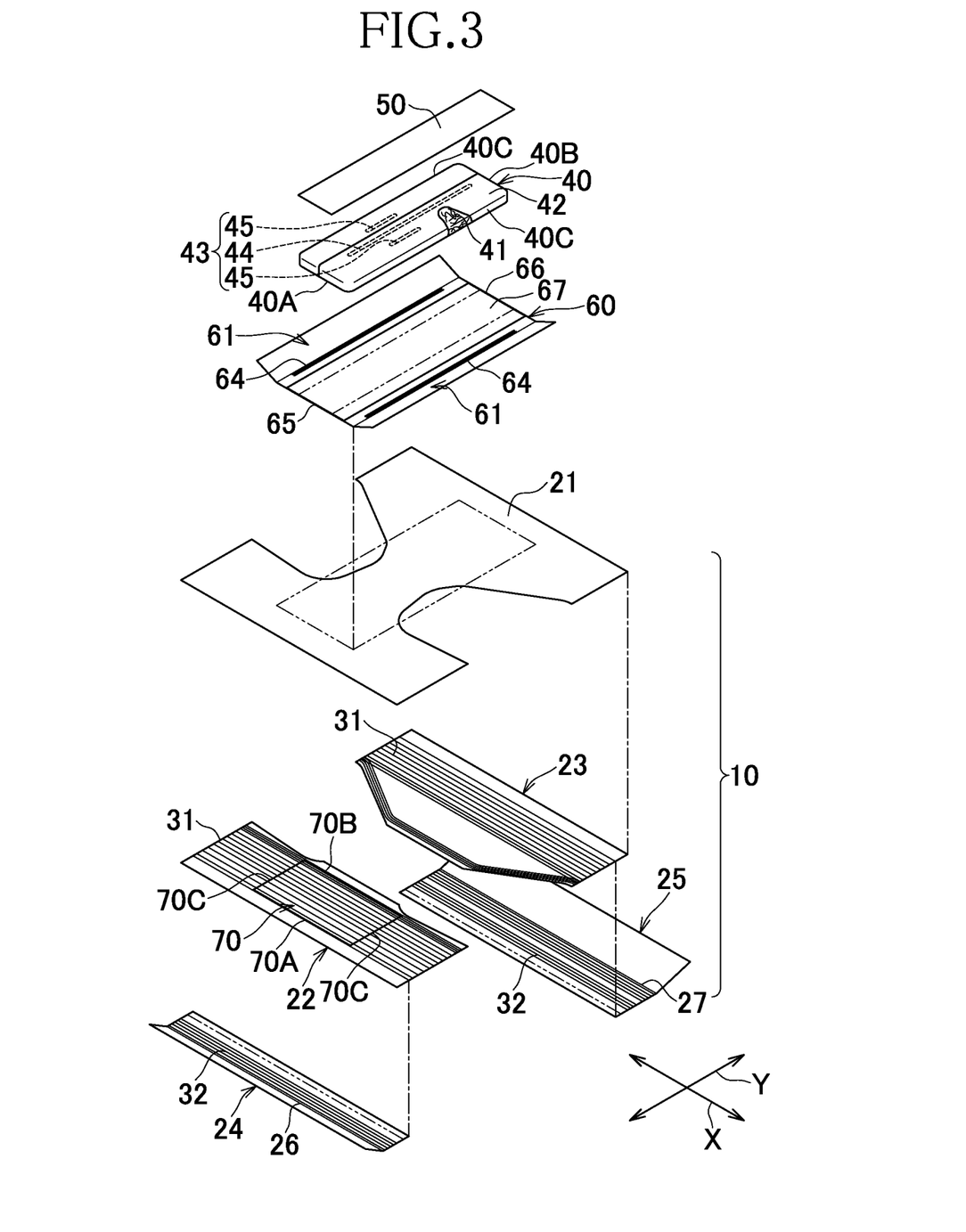
FIG. 3 is an exploded perspective view of the disposable diaper.

Referring to FIGS. 2 and 3, the diaper 1 has a longitudinal center line 2-2 bisecting a dimension in the transverse direction X and a transverse center line 3-3 bisecting a dimension in the longitudinal direction Y wherein the diaper 1 is symmetric about the longitudinal center line 2-2. In these FIGS. 2 and 3, respective elastic members are illustrated in a stretched state against their contractile force.

The chassis 10 includes a base sheet 21 lying on the non-skin-facing surface to define the front and rear waist regions 11, 12 and the crotch region 13, front and rear exterior sheets 22, 23 overlaid on the exterior surface side of the base sheet 21 so that these front and rear exterior sheets 22, 23 may be spaced apart from each other in the longitudinal direction Y, and front and rear waist end covers 24, 25 folded along fold lines 26, 27 extending in the transverse direction X so as to cover the base sheet 21 and the front and rear exterior sheets 22, 23, respectively. The front exterior sheet 22 defines the front waist region 11 and the rear exterior sheet 23 defines the rear waist region 12 and part of the crotch region 13. As material for the base sheet 21, the front and rear exterior sheets 22, 23 and the waist end covers 24, 25, various types of fibrous nonwoven fabrics, for example, heat-sealable spunbond fibrous nonwoven fabrics having a mass per unit area in a range of about 10 to about 40 g/m2, preferably in a range of about 13 to about 20 g/m2. a fiber density in a range of about 0.03 to about 0.10 g/m3, preferably in a range of about 0.04 to about 0.09 g/m3 may be used.

While the base sheet 21, the front and rear waist sheets 22, 23 in the present embodiment are respectively illustrated as monolayer sheets, an alternative embodiment is also possible in which the respective sheets include a plurality of layers, for example, a pair of nonwoven fabric layers, i.e., an interior nonwoven fabric layer and an exterior nonwoven fabric layer or a pair of sheets of which one may be nonwoven fabric sheets and the other may be plastic sheets.

Figure 4:
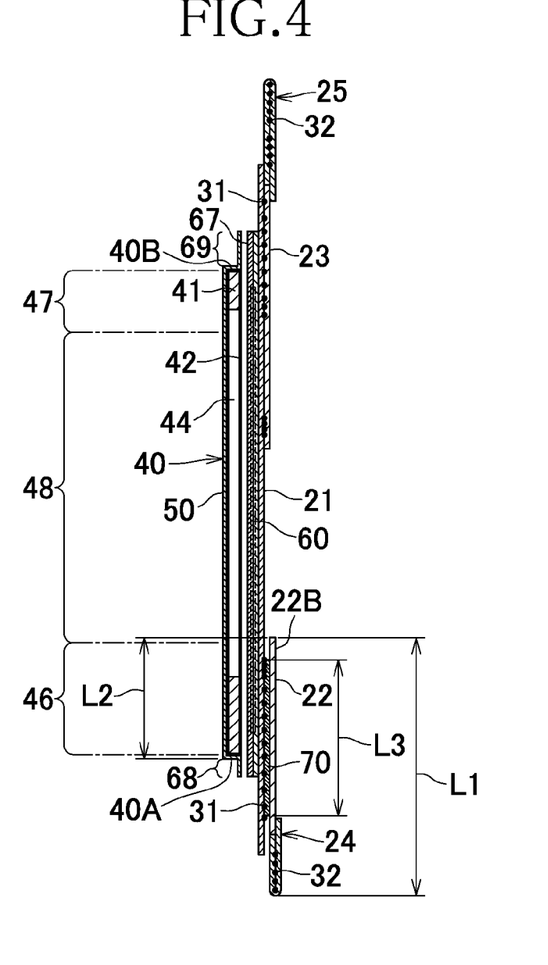
FIG. 4 is a sectional view taken along line IV-IV in FIG. 2.

Referring to FIG. 4 in addition, a plurality of elastic embers 31 extending in the transverse direction X are contractibly secured under tension between the base sheet 21 and the front and rear exterior sheets 22, 23.

The front and rear waist end covers 24, 25 are disposed within respective sleeves formed by folding the end covers 24, 25 with a plurality of elastic members 32 contractibly secured under tension so as to extend in the transverse direction X. As material for the elastic members 31, 32, for example, thread-, strand- or string-like elastic members having a fineness in a range of about 470 to about 1240 dtex may be used and may be secured, for example, at a stretch ratio in a range of about 1.5 to about 3.5.

On the inner surface of the base sheet 21, an absorbent structure 40 is disposed. The absorbent structure 40 includes front and rear end edges 40A, 40B extending in the transverse direction X, both side edges 40C extending in the longitudinal direction Y, liquid-absorbent core material 41 and a wrapping sheet 42 such as tissue paper to wrap the core material 41. The core material 41 is formed with recesses 43 each boring the core material 41 in its thickness direction and extending in the longitudinal direction Y. The recesses 43 include a central recess 44 extending in the longitudinal direction X along the longitudinal center line 2-2 across the crotch region 13 into the front and rear waist regions 11, 12 and a pair of lateral recesses 45 spaced apart outward from the central recess 44 in the transverse direction X. The lateral recesses 45 have a dimension in the longitudinal direction Y smaller than that of the central recess 44 and are biased toward the front waist region 11.

Figure 5:
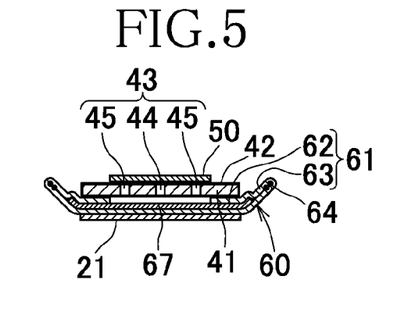
FIG. 5 is a sectional view taken along line V-V in FIG. 2.

A dimension in the transverse direction X of the central recess 44 and the lateral recesses 45 is preferably in a range of about 5 to about 20 mm and, for the present embodiment, this dimension is about 8 mm. A dimension in the longitudinal direction Y of the central recess 44 is preferably in a range of about 200 to about 400 mm and, for the present embodiment, this dimension is about 330 mm. A dimension in the longitudinal direction Y of the lateral recess 45 is preferably in a range of about 50 to 400 mm and, for the present embodiment, this dimension is about 80 mm. As the core material 41, a mixture of wood fluff pulp and superabsorbent polymer particles and optionally any other substances may be used. A mass per unit area of wood fluff pulp is preferably in a range of about 0 to 500 g/m2 and, for the present embodiment, this mass per unit area is about 300 g/m2. A mass per unit area of superabsorbent polymer particles is preferably in a range of about 0 to about 500 g/m2 and, for the present embodiment, this mass per unit area is about 250 g/m2. FIG. 5 illustrates the recesses 43, 44 in which the core material does not exist in the thickness direction, but a little amount of the core material may exist on bottoms of the recesses. The absorbent structure 40 may be disposed with the recesses 43, 44 to facilitate the absorbent structure 40 to bend along the recesses 43.44, thereby coming in close contact with the wearer and to absorb body exudates effectively. The presence of the central recess 44 and the lateral recesses 45 is particularly effective to bend the absorbent structure in a W-shape, thereby keeping a portion of the diaper in the vicinity of the longitudinal center line 2-2 along which the central recess 44 extends in close contact with the wearer's crotch region and to define pockets in the vicinity of the lateral recesses 45 so that the wearer's body exudates may be reliably collected in the pocket.

Referring again to FIGS. 2 and 3, the absorbent structure 40 extends in the longitudinal direction Y across the crotch region 13 into the front and rear waist regions 11, 12 to front and rear end edges 40A, 40B thereof lying in the front and rear waist regions 11, 12, respectively, and, in this way, includes a first region 46 defined in the front waist region 11, a second region 47 defined in the rear waist region 12 and a third region 48 defined in the crotch region 13 extending between them. Referring to FIG. 4 in addition, the central recess 44 extends across the third region 48 into the first and second regions 46, 47 and partially and indirectly overlaps the waist elastic members 31. The lateral recesses 45 are present only in the third region 48.

The term "indirectly overlaps" used herein means that the central recess 44 partially overlaps the waist elastic members 31 in a thickness direction of the diaper through the intermediary of the other constituents, for example, the base sheet 21 or, in addition to the base sheet 21, a barrier sheet 60 and a leakage-barrier sheet 67 as described later with reference to FIG. 4. In this regard, an alternative arrangement is also possible such that the waist elastic members 31 not through the intermediary of the base sheet 21, the barrier sheet 60 and the leakage-barrier sheet 67 but directly overlaps a bottom surface of the absorbent structure 40, i.e., overlaps the central recess 44 in the thickness direction of the diaper between the bottom surface and the leakage-barrier sheet 67.

Figure 6:
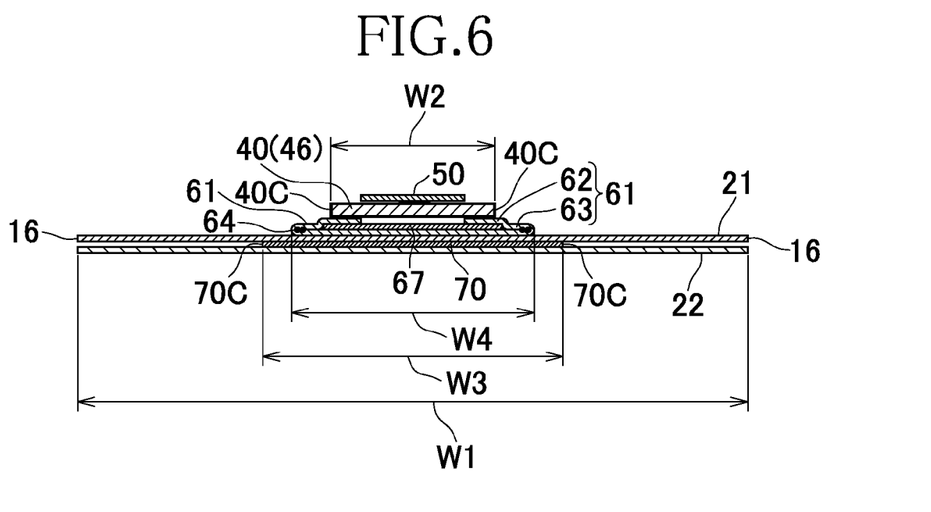
FIG. 6 is a sectional view taken along line VI-VI in FIG. 2.

Referring to FIG. 6 in addition, a dimension W2 in the transverse direction X of the first region 46 is preferably in a range of about 20 to about 30% of a dimension W1 in the transverse direction X of the front waist region 11. For the present embodiment, the dimension W2 in the transverse direction X of the first region 46 of the absorbent structure 40 is about 135 mm, the dimension W1 in the transverse direction X of the front waist region 11 is about 580 mm and the dimension W2 is about 23% of the dimension W1.

Referring to FIGS. 2 and 4, a dimension L2 in the longitudinal direction Y of the front end portion 46 is preferably in a range of about 30 to about 60% of a dimension L1 in the longitudinal direction Y of the front waist region 11. For the present embodiment, the dimension L2 in the longitudinal direction Y of the front end portion 46 of the absorbent structure 40 is about 100 mm, the dimension L1 in the longitudinal direction Y is about 230 mm and the dimension L2 is about 43% of the dimension L1.

Considering that the dimension W2 is usually about 30% or more of the dimension W1 and the dimension L2 is usually about 60% or more, the dimension of the front end portion 46 is relatively small in the diaper 1 for the present embodiment.

The dimensions in the longitudinal direction Y and the transverse direction X of the front waist region 11 and the first region 46 of the absorbent structure 40 are measured in the state in which the respective sheets defining the front waist region 11 and the first region 46 are flattened against the contractile forces of the elastic members 31, 32 and cuff-elastic members 64 as described hereunder.

The absorbent structure 40 is disposed on an absorbent surface with a body-side liner 50 and on a bottom surface thereof with a barrier sheet 60 adapted to define gasket-cuffs 61. Referring to FIG. 6, the barrier sheet 60 has both laterals adapted to be folded back, thereby forming sleeves within which respective cuff-elastic members 64 extend in the longitudinal direction Y and are contractibly secured under tension. In this way, the gasket-cuffs 61 are formed. The gasket-cuffs 61 include, in regions thereof overlapping with the absorbent structure 40, a pair of proximal portions 62 bonded to the absorbent structure 40 and the interior sheet 21 and, in regions thereof extending outward in the transverse direction X from both side edges 40c thereof, a pair of distal portions 63 not bonded to the interior sheet 21. The cuff-elastic members 64 are present in the distal portions 63 and, under contractile force thereof, the distal portions 63 are separated from the interior sheet 21 toward the crotch of the diaper wearer. The gasket-cuffs 61 further include front and rear end portions 65, 66 extending in the transverse direction X which are bonded to the interior sheet 21 on the outer sides in the transverse direction X of the absorbent structure 40.

With the gasket-cuffs 61 described above, the distal portions 63 are spaced apart upward from the interior sheet 21 under the contractile force of the cuff-elastic members 64 so as to be put in close contact with thighs of the wearer thereby preventing body exudates from leaking (See FIG. 5).

A dimension in the longitudinal direction Y of the barrier sheet 60 is larger than that of the absorbent structure 40. In consequence, on the outside in the longitudinal direction Y of the front and rear end edges 40A, 40B, the barrier sheet 60 and the body-side liner 50 are disposed with first and second flaps 68, 69 in which the core material is not present. In the first and second end flaps 68, 69, the barrier sheet 60 and the body-side liner 50 are joined to each other preferably in a watertight manner. The first and second end flaps 68, 69 respectively lie in the front and rear waist regions 11, 12 and a dimension in the longitudinal direction Y of the first end flap 68 is preferably larger than that of the second end flap 69. For the present embodiment, the dimension in the longitudinal direction Y of the first end flap 68 is about 20 mm and the dimension in the longitudinal direction Y of the second flap 69 is about 35 mm.

The aged wearers often spend a great deal of time in supine posture and, as an inevitable consequence, an amount of body exudates absorbed by the second region 47 of the absorbent structure 40 lying I the rear waist region 12 is larger than that absorbed by the first region 46. The core material of the absorbent structure 40 is swollen as it absorbs body exudates, for example, urine and there is a possibility that the amount of urine once absorbed by the absorbent structure 40 might leak through the second end flap 69 when the second region 47 swollen in this manner is pressed down by the wearer's buttocks or waist. However, the second end flap 69 may be dimension to be relatively large as the present embodiment to prevent such leakage. To prevent such leakage through the second end flap 69, the dimension in the longitudinal direction Y of the second end flap 69 is preferably at least about 25 mm or more.

Between the barrier sheet 60 and the absorbent structure 40, the leakage-barrier sheet 67 formed of breathable plastic films is disposed to prevent body exudates once having been absorbed in the absorbent structure 40 from leaking out therefrom. The leakage-barrier sheet 67 extends outward in the transverse direction X from the absorbent structure 40 but is disposed on the inside of the cuff-elastic members 64. With such an arrangement, it is possible to avoid a possibility that regions of the respective distal portions 63 including the cuff-elastic members 64 might have stiffness increased due to the leakage-barrier sheet 67, thereby protecting the wearer's skin against uncomfortable irritation.

The shape retention panel 70 has front and rear end edges 70A, 70B extending in the transverse direction X and both side edges 70C extending in the longitudinal direction Y and is disposed so as to overlap the first region 46 of the absorbent structure 40 in an indirect manner as viewed in the thickness direction of the diaper. The term "indirectly overlaps" used herein means that the shape retention panel 70 overlaps the first region 46 of the absorbent structure 40 in the thickness direction of the diaper through the intermediary of the other constituents such as the base sheet 21, barrier sheet 60 and the leakage-barrier sheet 67. In this regard, an alternative arrangement is also possible such that the shape retention panel 70 not through the intermediary of the base sheet 21, the barrier sheet 60 and the leakage-barrier sheet 67 but directly overlaps a bottom surface of the absorbent structure 40, i.e., overlaps the first region 46 of the absorbent structure 40 in the thickness direction of the diaper between the bottom surface and the leakage-barrier sheet 67. Referring to FIGS. 2 and 6, the side edges 70C are disposed on the outside of the respective side edges 40C of the absorbent structure 40 as viewed in the transverse direction X and on the outside of the distal portions 63. More specifically, a dimension W3 in the transverse direction X of the shape retention panel 70 is preferably larger than the dimension W2 of the first region 46 and larger than a dimension W4 in the transverse direction X between the pair of the distal portions 63. In the present embodiment, the dimension W3 is about 260 mm and the dimension W4 is about 200 mm.

Referring to FIGS. 2 and 4, a dimension L3 in the longitudinal direction Y of the shape retention panel 70 is preferably larger than the dimension L2 of the first region 46 of the absorbent structure 40. For the present embodiment, the dimension L3 is about 160 mm. The dimensions in the longitudinal direction Y and the transverse direction X of the shape retention panel 70 are the dimension in the longitudinal direction Y of both side edges 70C and the dimension in the transverse direction X of the front end edge 70A measured in a state of the shape retention panel 70 having been flatly developed in the longitudinal direction Y and the transverse direction X against contractile force of the waist elastic members 31, 32 and the cuff-elastic members 64.

Referring again to FIG. 6, in both side edge portions 16 of the front waist region 11, the base sheet 21 and the front waist sheet 22 are laminated and, in a central portion in the transverse direction X of the front waist region 11, the shape retention panel 70 is bonded between the two sheets 21, 22. On the inner side of the central portion in the transverse direction X, the gasket cuffs 61 are bonded to the base sheet 21 and, on the further inner side in the transverse direction X of the gasket cuffs 61, the leakage-barrier sheet 67 and the absorbent structure 40 are laminated in addition to the sheets. In this manner, from both side edges 16 toward the inner side as viewed in the transverse direction X, the number of the constituent members to be laminated gradually increases. The front waist region 11 has the elastic members 31 extending in the transverse direction X and secured thereto and the front waist region 11 as a whole constricts in the transverse direction X under contraction of the elastic members 31. Compared to the third region 53 merely defined by the laminate of the base sheet 21 and the front waist sheet 22, the first region 51 additionally includes the absorbent structure 40 laminated on the base sheet 21 and the front waist sheet 22 has correspondingly higher stiffness. If the second regions 52 are not present, a differential stiffness will be apt to create sharp difference in level between the first region 51 and the third regions 53 as the sheets constrict and a desired effect of close contact with the wearer's skin will be deteriorated. However, for the present embodiment, the respective second regions 52 in which the barrier sheet 60 and the shape retention panel 70 are laminated are disposed on the outsides in the transverse direction X of the absorbent structure 40 so that the stiffness may increase stepwise from the outside toward the inside in the transverse direction X. In this way, the differential stiffness relative to the existence region of the absorbent structure 40 may be reduced. In this way, it is possible to restrict a possibility that a sharp difference in level might be formed due to contraction of the elastic members.

An average bending stiffness B1 in the transverse direction X of the region in which the base sheet 21, the front waist sheet 22 and the shape retention panel 70 overlap with each other is preferably in a range of about 0.4 to about 1.2 gf×cm/cm and, for the present embodiment, in a range of about 0.65 gf×cm/cm. An average bending stiffness B2 in the transverse direction X of the region not including the shape retention panel 70, i.e., defined by only the laminate of the base sheet 21 and the front waist sheet 22 is in a range of about 0.2 to about 0.6 gf×cm/cm and, for the present embodiment, in a range of about 0.28 gf×cm/cm. In this manner, it is possible to enhance the bending stiffness particularly in the transverse direction X by laminating the shape retention panel 70, thereby lessening a differential stiffness relative to the absorbent structure 40 and to restrict formation of any sharp difference in level due to contraction of the elastic members 31.

An average bending stiffness B1 in the transverse direction X of the second region 52 is preferably in a range of about 150 to about 300% of an average bending stiffness B2 of the third region 53. For the present embodiment, the average bending stiffness B1 is about 232% of the average bending stiffness B1. When the average differential bending stiffness between the regions is higher than 300%, there is a possibility that a sharp difference in level might be created between the regions due to contraction of the elastic members and when the average differential bending stiffness is less than 150%, a stiffness of the diaper 1 as a whole will increase and a desired flexibility may be deteriorated.

<Measuring Method for Bending Stiffness>

The bending stiffness was measured with use of Pure Bending Tester KES FB-2 manufactured by KATO TECH CO., LTD. From common regions of the diapers 1, test pieces each having a dimension in the longitudinal direction Y of 50 mm and having a dimension in the transverse X of 100 mm and test pieces each having a dimension in the longitudinal direction Y of 100 mm and a dimension in the transverse direction X of 50 mm were prepared. One end in the longitudinal direction of the test piece was held by one of a pair of chucks and the end in the longitudinal direction of the test piece was held by the other chuck. The test piece was bent as the one chuck was rotated around the other chuck so as to bend the test piece and then a bending stiffness of this test piece was measured with use of a torque detector. The bending stiffness was measured more than once for each test piece and an average value was calculated for each test piece. Then two groups of test pieces each including five test pieces were prepared and average measurement values were recorded as the average bending stiffness (B1, B2) in the transverse direction X. Considering that the front waist region 11 used for the measurement includes the elastic members 31 secured thereto under tension, the front waist region 11 was flatly developed in the longitudinal direction Y as well as in the transverse direction X against the contractile force of these elastic members for making the measurement.

The shape retention panel 70 may be disposed so as to overlap the first region 46 of the absorbent structure 40 to enhance stiffness in the first region 46, thereby preventing the absorbent structure 40 from contracting in the transverse direction X under contraction of the waist elastic members 31. Whereby it is possible to prevent the recesses 43 extending in the first region 46, particularly the central recess 44 from unacceptably contracting in the transverse direction X and to maintain the original configuration of the recesses 43. If the recesses 43 contract in the transverse direction X so significantly that it becomes impossible to maintain their original configuration, it will be impossible for the absorbent structure 40 to be bent along the recesses 43 and to be put in close contact with the wearer's skin. The present embodiment makes it possible to prevent such problem. Furthermore, formation of the recesses makes it possible to enlarge the absorbent area of the absorbent structure 40 and also to prevent an area loss of the absorbent area as far as the configurations of the recesses are maintained. Arrangement of the central recess 44 so as to extend into the front end portion 46 makes it possible to keep the absorbent structure 40 in close contact with the wearer's skin in the front waist region 11, thereby preventing body exudates from leaking from the front waist region 11.

According to the present embodiment, an inner end portion 22B of the front waist sheet 22 in the crotch region 13 is curved toward the longitudinal center line 2-2 so that the apparent dimension thereof in the longitudinal direction Y may be reduced. Considering that the inner end portion 22B is the portion defining the leg-openings and to be kept in close but not excessively tight contact with the wearer's thighs, the inner end portion 22B is curved in conformity to the wearer's thighs. With such an arrangement, the shape retention panel 70 is disposed further outside the region of the inner end portion 22B lying at the outermost position in the longitudinal direction Y. In this way, it is possible to prevent the shape retention panel 70 from coming in contact with the wearer's skin. The dimension between both side edges 70C of the shape retention panel 70 is dimensioned to be larger than the minimum dimension in the transverse direction X of the chassis 10, i.e., the dimension in the transverse direction X of the crotch region 13 in the present embodiment. With such dimensioning, it is possible to prevent the shape retention panel 70 from coming in contact with the wearer's skin in the transverse direction X also.

As material for the shape retention panel 70, for example, moisture-permeable but liquid-impermeable plastic films having a mass per unit area in a range of about 10 to about 30 g/m2, preferably in a range of about 14 to about 25 g/m2 may be used. More specifically, plastic films of polyolefin resin mixed with inorganic filler such as titanium oxide and subjected to stretching process may be used. While it is not essential for the plastic films to be breathable and liquid-impermeable, use of liquid-impermeable plastic films makes it possible to enhance the preventive effect against leakage of body exudates. As material for the shape retention panel, it is also possible to use fibrous nonwoven fabrics or laminates of fibrous nonwoven fabrics and plastic films. The fibrous nonwoven fabrics used for the shape retention panel may be liquid-permeable or liquid-impermeable.

While the recesses 45 are disposed so as to be biased toward the front waist region 11, it is also possible to disposed the recesses 45 so as to extend into the rear waist region 12 or to extend into both waist regions 11, 12. Correspondingly, it is possible to dispose the shape retention panel 70 in the rear waist region 12 or to locate a pair of the shape retention panels 70 in the front and rear waist regions, respectively. While the present embodiment has been described hereinabove with respect to pants-type (pull-on) disposable diapers, the present invention is applicable also to open-type disposable diapers of which both side edges are left open.

The disclosure relating to the present invention as has been described hereinabove may be arranged at least as follows:

A wearing article has a longitudinal direction Y parallel to a longitudinal center line 2-2, a transverse direction X parallel to a transverse center line 3-3, a skin-facing surface and a non-skin-facing surface opposite to the skin-facing surface, and includes a chassis 10 having a first waist region 11 defined by one of front and rear waist regions 11, 12 and being elastically contractible in the transverse direction X, a second waist region 12 defined by the other of the front and rear waist regions 11, 12 and a crotch region 13 lying between the front and rear waist regions 11, 12, an absorbent structure 40 disposed on the skin-facing surface of the chassis 10 and extending in the longitudinal direction Y across the crotch region 13 into at least the first waist region 11 and recesses 43 disposed on the absorbent structure 40.

In the wearing article as has been described above, the present invention lies in the following features:

the absorbent structure 40 includes a first region 46 defined in the first waist region 11 and the recesses at least partially lying in the first region 46 and extending in the longitudinal direction Y; and a shape retention panel 70 is disposed on the non-skin-facing surface of the first waist region 11 so that the shape retention panel 70 indirectly or directly overlap the first region 46 and the recesses 43 as viewed in a thickness direction of the article.

The present invention may include at least the following embodiments:

(1) The absorbent structure 40 further includes a second region 47 defined in the second waist region 12 and a third region 48 defined between the first and second regions 46, 47.

(2) The shape retention panel 70 has first and second end edges 70A, 70B extending in the transverse direction X and both side edges 70C extending in the longitudinal direction Y; and the side edges 70C lie on the outside in the transverse direction X of both side edges 40C of the first region 46 extending in the longitudinal direction Y.

(3) The recesses 43 include a central recess 44 extending along the longitudinal center line 2-2 and lateral recesses 45 lying on the outsides in the transverse direction X of the central recess 44.

(4) The central recess 44 has opposite end portions in the longitudinal direction Y thereof in the first and second regions 46, 47, respectively, and a remaining portion in the third region 48.

(5) A dimension in the longitudinal direction Y of the central recess 44 is larger than that of the lateral recesses 45 and at least part of the central recess 44 lies in the first region 46.

(6) The lateral recesses 45 are disposed so as to be biased toward the side of the first waist region 11.

(7) The first waist region 11 includes a plurality of waist-elastic members 31 extending in the transverse direction X and contractibly secured thereto under tension and at least part of the waist elastic members 31 indirectly or directly overlaps the recesses 43 as viewed in a thickness direction of the article.

(8) The absorbent structure 40 includes liquid-absorbent core material 41 and a wrapping sheet 42 to wrap the core material 41;

on the outsides in the longitudinal direction of the absorbent structure 40, first and second end flaps 68, 69 both being core material non-existence regions are defined in the first and second waist regions 11, 12; and a dimension in the longitudinal direction Y of the second end flap 69 is smaller than that of the first end flap 68.

(9) The shape retention panel 70 has the first end edge 70A thereof lying on the outside in the longitudinal direction Y of the first region 46 of the absorbent structure 40.

(10) An average bending stiffness in the transverse direction X of a zone in the first waist region 11 in which the shape retention panel 70 is disposed is in a range of about 0.4 to about 1.2 gf·cm/cm and an average bending stiffness in the transverse direction X of a zone in which the shape retention panel 70 is not present is in a range of about 0.2 to about 0.6 gf·cm/cm.

The constituent members of the disposable diaper are not limited to those described in the specification but the other various types of material widely used in the relevant technical field may be used without limitation. The diaper as an example of the wearing article is not limited to the diaper according to the present embodiment but may also by open-type diapers having the front and rear waist regions not joined to each other along seams.

The present invention is applicable to the wearing articles such as toilet-training pants, incontinent pants, sanitary pants and absorbent pads.

Terms "first" and "second" used in the specification and claims of this invention are used merely to distinguish the similar elements, similar positions or the other similar items.

REFERENCE SIGNS LIST 2-2 longitudinal center line
10 chassis
11 front waist region (one of first of second waist regions)

12 rear waist region (the other of first and second waist regions)
13 crotch region
31 waist-elastic members
40 absorbent structure
41 core material
42 wrapping sheet
43 recesses
44 central recess
45 both side recesses
46 first region
47 second region
48 third region
49 first end flap
69 second end flap
70 shape retention panel
70A front end edge (first end edge)
70B rear end edge (second end edge)
70C both side edges
X transverse direction
Y longitudinal direction

The invention claimed is:

1. A wearing article having a longitudinal direction parallel to a longitudinal center line, a transverse direction parallel to a transverse center line, a skin-facing side and a non-skin-facing side opposite to the skin-facing side, and including:
a chassis having:
a first waist region defined by one of front and rear waist regions and being elastically contractible in the transverse direction,
a second waist region defined by another of the front and rear waist regions, the first and second waist regions being joined together along transverse seams and
a crotch region lying between the front and rear waist regions; and
an absorbent structure disposed on the skin-facing side of the chassis and extending in the longitudinal direction across the crotch region into at least the first waist region and recesses disposed on the absorbent structure,
a plurality of waist-elastic members in the first waist region which extend in the transverse direction, wherein:
the absorbent structure includes a first region defined in the first waist region and the recesses at least partially lying in the first region and extending in the longitudinal direction; and
a shape retention panel is disposed on the non-skin-facing side of the first waist region so that the shape retention panel indirectly or directly overlap the first region and the recesses as viewed in a thickness direction of the article;
the shape retention panel has first and second end edges extending in the transverse direction and opposed side edges extending in the longitudinal direction;
the second end edge of the shape retention panel is disposed within the front waist region near a front end of the crotch region;
the opposed side edges of the shape retention panel are transversely disposed outward from respective longitudinal side edges of the first region and the first end edge of the shape retention panel is disposed longitudinally outward of the first region;
a part of an inner end edge of the first waist region disposed on the outside of the absorbent structure as viewed in the transverse direction has a concave shape toward the crotch region;
the second end edge of the shape retention panel is disposed on the outside of the inner end edge of the first waist region as viewed in the longitudinal direction;
the shape retention panel is located on the non-skin-facing surface of the plurality of waist-elastic members;
the recesses include a central recess extending along the longitudinal center line and lateral recesses lying outside of the central recess in the transverse direction;
a dimension in the longitudinal direction of the central recess is larger than that of the lateral recesses and at least part of the central recess lies in the first region;
a dimension in the transverse direction of the central recess and the lateral recesses is in a range of 5 to 20 mm and a dimension in the longitudinal direction of the central recess is in a range of 200 to 400 mm and a dimension in the longitudinal direction of the lateral recess is in a range of 50 to 400 mm; and
a part of an inner end edge of the second waist region disposed on the outside of the absorbent structure as viewed in the transverse direction extends linearly downward from a lower end of the seams toward the absorbent structure.

2. The wearing article according to claim 1 wherein the absorbent structure further includes a second region defined in the second waist region and a third region defined between the first and second regions.

3. The wearing article according to claim 1, wherein the central recess has opposite end portions in the longitudinal direction thereof in the first and second regions, respectively, and a remaining portion in the third region.

4. The wearing article according to claim 1, wherein the lateral recesses are disposed so as to be biased toward the side of the first waist region.

5. The wearing article according to claim 1, wherein the plurality of waist-elastic members are contractibly secured to the first waist region under tension and at least part of the waist elastic members indirectly or directly overlaps the recesses as viewed in a thickness direction of the article.

6. The wearing article according to claim 1, wherein
the absorbent structure includes liquid-absorbent core material and a wrapping sheet to wrap the core material;
on the outsides in the longitudinal direction of the absorbent structure, first and second end flaps both being core material non-existence regions are defined in the first and second waist regions; and
a dimension in the longitudinal direction of the second end flap is smaller than that of the first end flap.

7. The wearing article according to claim 1, wherein an average bending stiffness in the transverse direction of a zone in the first waist region in which the shape retention panel is disposed is in a range of about 0.4 to about 1.2 gf·cm/cm and an average bending stiffness in the transverse direction of a zone in which the shape retention panel is not present is in a range of about 0.2 to about 0.6 gf·cm/cm.

* * * * *

UNITED STATES PATENT AND TRADEMARK OFFICE
CERTIFICATE OF CORRECTION

PATENT NO. : 10,064,764 B2
APPLICATION NO. : 14/397621
DATED : September 4, 2018
INVENTOR(S) : Yusuke Kawakami and Kazuya Fujimoto It is certified that error appears in the above-identified patent and that said Letters Patent is hereby corrected as shown below:

In the Specification

Column 3, Line 26 should be changed from "40 g/m2" to --40 $g/m^2$--

Column 3, Line 26 should be changed from "20 g/m2" to --20 $g/m^2$--

Column 3, Line 27 should be changed from "0.10 g/m3" to --0.10 $g/m^3$--

Column 3, Line 28 should be changed from "0.09 g/m3" to --0.09 $g/m^3$--

Column 4, Line 14 should be changed from "500 g/m2" to --500 $g/m^2$--

Column 4, Line 16 should be changed from "g/m2" to --$g/m^2$--

Column 4, Line 19 should be changed from "250 g/m2" to --250 $g/m^2$--

Column 9, Line 8 should be changed from "30 g/m2" to --30 $g/m^2$--

Column 9, Line 8 should be changed from "25 g/m2" to --25 $g/m^2$--

Signed and Sealed this
Twelfth Day of February, 2019

Andrei Iancu
*Director of the United States Patent and Trademark Office*